United States Patent [19]

Robinson

[11] 4,362,653

[45] Dec. 7, 1982

[54] HYDROCARBON CONVERSION CATALYST

[75] Inventor: Delmar W. Robinson, Palatine, Ill.

[73] Assignee: UOP Inc., Des Plaines, Ill.

[21] Appl. No.: 257,690

[22] Filed: Apr. 27, 1981

[51] Int. Cl.³ .............................................. B01J 21/12
[52] U.S. Cl. ................................................ 252/455 R
[58] Field of Search ........................ 252/455 R, 455 Z

[56] References Cited

U.S. PATENT DOCUMENTS

| | | | |
|---|---|---|---|
| 2,892,858 | 6/1959 | Ziegler et al. | 260/448 |
| 2,999,074 | 9/1961 | Bloch et al. | 252/442 |
| 3,852,190 | 12/1974 | Buss et al. | 208/138 |
| 4,012,313 | 3/1977 | Buss et al. | 208/139 |
| 4,061,724 | 12/1977 | Grose et al. | 423/335 |
| 4,309,275 | 1/1982 | Mulaskey | 252/455 R |
| 4,309,276 | 1/1982 | Miller | 252/455 R |

FOREIGN PATENT DOCUMENTS 2051853  1/1981  United Kingdom .

Primary Examiner—Carl F. Dees
Attorney, Agent, or Firm—James R. Hoatson, Jr.; John G. Cutts, Jr.; William H. Page, II

[57] ABSTRACT

Hydrocarbons are converted by contacting them at hydrocarbon conversion conditions with a catalyst composite comprising a silica polymorph consisting of crystalline silica, said silica polymorph after calcination in air at 600° C. for one hour, having a mean refractive index of 1.39±0.01 and a specific gravity at 25° C. of 1.70±0.05 g/cc and a refractory inorganic oxide.

2 Claims, No Drawings

HYDROCARBON CONVERSION CATALYST

BACKGROUND OF THE INVENTION

This invention relates to a catalyst and a process for the conversion of hydrocarbons. The subject of the present invention is a novel catalytic composite which has exceptional activity, selectivity and resistance to deactivation when employed in a hydrocarbon conversion process. The present invention, more precisely, involves a novel catalyst composite comprising a silica polymorph consisting of crystalline silica, said silica polymorph after calcination in air at 600° C. for one hour, having a mean refractive index of 1.39±0.01 and a specific gravity at 25° C. of 1.70±0.05 g/cc and a refractory inorganic oxide.

Composites having a catalyst function are widely used today as catalysts in many industries, such as the petroleum and petrochemical industry, to accelerate a wide spectrum of hydrocarbon conversion reactions. These catalytic composites are used to accelerate a wide variety of hydrocarbon conversion reactions such as hydrocracking, hydrogenolysis, isomerization, dehydrogenation, hydrogenation, alkylation, dimerization, cracking, hydroisomerization, dealkylation, transakylation, reforming, dehydrocyclodimerization, etc. In many cases, the commercial applications of these catalysts are in processes where more than one of the reactions are proceeding simultaneously. An example of this type of process is reforming wherein a hydrocarbon feed stream containing paraffins and naphthenes is subjected to conditions which promote dehydrogenation of naphthenes to aromatics, dehydrocyclization of paraffins to aromatics, isomerization of paraffins and naphthenes, hydrocracking and hydrogenolysis of naphthenes and paraffins, and the like reactions, to produce an octane-rich or aromatic-rich product stream. Another example is a hydrocracking process wherein catalysts of this type are utilized to effect selective hydrogenation and cracking of high molecular weight unsaturated materials, selective hydrocracking of high molecular weight materials, and other like reactions, to produce a generally lower boiling, more valuable output stream. Yet another example is a hydroisomerization process wherein a hydrocarbon fraction which is relatively rich in straight-chain paraffin compounds is contacted with a catalyst to produce an output stream rich in isoparaffin compounds.

Another example is a hydroisomerization process wherein an alkylaromatic hydrocarbon fraction is contacted with a catalyst to enhance the quantity of a selected alkylaromatic isomer.

Regardless of the reaction involved or the particular process involved, it is of critical importance that the catalyst exhibit not only the capability to initially perform its specified functions, but also that it has the capability to perform them satisfactorily for prolonged periods of time. The analytical terms used in the art to measure how well a particular catalyst performs its intended functions in a particular hydrocarbon reaction environment are activity, selectivity, and stability. For purposes of discussion here, these terms are conveniently defined for a given charge stock as follows: (1) activity is a measure of the catalyst's ability to convert hydrocarbon reactants into products at a specified severity level where severity level means the conditions used—that is, the temperature, pressure, contact time, and presence of diluents such as hydrogen; (2) selectivity refers to the amount of desired product or products obtained relative to the amount of reactants charged or converted; (3) stability refers to the rate of change with time of the activity and selectivity parameters—obviously, the smaller rate implying the more stable catalyst. In a reforming process, for example, activity commonly refers to the amount of conversion that takes place for a given charge stock at a specified severity level and is typically measured by octane number of the $C_5+$ product stream; selectivity refers to the amount of $C_5+$ yield, relative to the amount of the charge that is obtained at the particular activity or severity level; and stability is typically equated to the rate of change with time of activity, as measured by octane number of $C_5+$ product, and of selectivity as measured by $C_5+$ yield. Actually, the last statement is not strictly correct because generally a continuous reforming process is run to produce a constant octane $C_5+$ product with severity level being continuously adjusted to attain this result; and furthermore, the severity level is for this process usually varied by adjusting the conversion temperature in the reaction zone so that, in point of fact, the rate of change of activity finds response in the rate of change of conversion temperatures and changes in this last parameter are customarily taken as indicative of activity stability.

As is well known to those skilled in the art, the principal cause of observed deactivation or instability of a catalyst when it is used in a hydrocarbon conversion reaction is associated with the fact that coke forms on the surface of the catalyst during the course of the reaction. More specifically, in these hydrocarbon conversion processes, the conditions utilized typically result in the formation of heavy, high molecular weight, black, solid or semi-solid, carbonaceous material which is a hydrogen deficient polymeric substance having properties akin to both polynuclear aromatics and graphite. This material coats the surface of the catalyst and thus reduces its activity by shielding its active sites from the reactants. In other words, the performance of this catalyst is sensitive to the presence of carbonaceous deposits or coke on the surface of the catalyst. Accordingly, the major problem facing workers in this area of the art is the development of more active and/or selective catalytic composites that are not as sensitive to the presence of these carbonaceous materials and/or have the capability to suppress the rate of the formation of these carbonaceous materials on the catalyst. Viewed in terms of performance parameters, the problem is to develop a catalyst having superior activity, selectivity, and stability characteristics. In particular, for a reforming process, the problem is typically expressed in terms of shifting and stabilizing the $C_5+$ yield-octane relationship at the lowest possible severity level—$C_5+$ yield being representative of selectivity and octane being proportional to activity.

I have discovered a catalyst composite which possesses improved activity, selectivity and stability characteristics when it is employed in a process for the conversion of hydrocarbons such as isomerization, hydroisomerization, dehydrogenation, desulfurization, denitrogenization, hydrogenation, alkylation, dealkylation, disproportionation, polymerization, hydrodealkylation, transalkylation, cyclization, dehydrocyclization, cracking, hydrocracking, halogenation, reforming, and the like processes.

BRIEF SUMMARY OF THE INVENTION

In summary, the present invention relates to a hydrocarbon conversion process wherein hydrocarbons are contacted at hydrocarbon conversion conditions with a catalyst composite comprising a silica polymorph consisting of crystalline silica, said silica polymorph after calcination in air at 600° C. for one hour, having a mean refractive index of 1.39±0.01 and a specific gravity at 25° C. of 1.70±0.05 g/cc and a refractory inorganic oxide.

DETAILED DESCRIPTION OF THE INVENTION

It is one object of the present invention to provide a hydrocarbon conversion catalyst having superior performance characteristics when utilized in a hydrocarbon conversion process. A second object is to provide a catalyst having conversion performance characteristics that are relatively insensitive to the deposition of hydrocarbonaceous material thereon. A third object is to provide a catalyst with outstanding characteristics toward transalkylation and dealkylation of ethylbenzene to alternate aromatics while simultaneously accomplishing equilibrium isomerization of xylenes in a process for the conversion of a feedstock containing ethylbenzene and a non-equilibrium mixture of xylenes. Another object is to provide a process for the conversion of hydrocarbons into more valuable or more desirable hydrocarbon products. Another object of the present invention is to teach a method of preparing a hydrocarbon conversion catalyst which comprises a silica polymorph consisting of crystalline silica, said silica polymorph after calcination in air at 600° C. for one hour, having a mean refractive index of 1.39±0.01 and a specific gravity at 25° C. of 1.70±0.05 g/cc and a refractory inorganic oxide. A first embodiment of the present invention is a catalyst composite comprising a silica polymorph consisting of crystalline silica, said silica polymorph after calcination in air at 600° C. for one hour, having a mean refractive index of 1.39±0.01 and a specific gravity at 25° C. of 1.70±0.05 g/cc and a refractory inorganic oxide. Another embodiment involves a process for the conversion of a hydrocarbon which comprises contacting the hydrocarbon and hydrogen with the catalyst composite defined in the first embodiment at hydrocarbon conversion conditions.

A highly preferred embodiment comprehends a process for isomerizing an admixture of alkylaromatic hydrocarbons which comprises contacting the alkylaromatic hydrocarbons and hydrogen with the catalyst composite described above in the first embodiment at isomerization conditions to produce an isomerized alkylaromatic product.

Other objects and embodiments of the present invention relate to additional details regarding preferred catalytic ingredients, preferred amounts of ingredients, suitable methods of composite preparation, operating conditions for use in the hydrocarbon conversion processes, and the like particulars, which are hereinafter given in the following detailed discussion of each of these facets of the present invention.

The catalyst composite of the present invention comprises a silica polymorph consisting of crystalline silica, said silica polymorph after calcination in air at 600° C. for one hour, having a mean refractive index of 1.39±0.01 and a specific gravity at 25° C. of 1.70±0.05 g/cc and a refractory inorganic oxide.

Considering first the crystalline silica from which the catalyst composite used in the present invention is made, it has been characterized in U.S. Pat. No. 4,061,724 as a crystalline silica composition having uniform pore dimensions of approximately 6 Angstrom units and is prepared by calcining a crystalline hydrated alkylonium silicate prepared hydrothermally from a reaction mixture containing as essential reagents, water, amorphous silica and a quaternary ammonium compound at a pH of at least 10. It is presently available from the Union Carbide Corporation and is referred to as E L Z-115 or silicalite. It is a crystalline silica material which exhibits some characteristics of conventional molecular sieves but does not have ion-exchange properties similar to aluminosilicate zeolites because its structure is composed entirely of silica. The crystalline silica material has excellent steam, thermal and acid stability. Further details, characteristics and methods of preparation are available in U.S. Pat. No. 4,061,724.

According to my invention, the hereinabove described silicalite is admixed with a separate and distinct refractory inorganic oxide. In addition to the crystalline silica, another material classified as a refractory inorganic oxide is essential to my invention. It is acknowledged that silicalite is a type of refractory inorganic oxide but for purposes of this description the term "refractory inorganic oxide" excludes silicalite. This definition is required to afford a generic description of material which may be admixed with silicalite for the practice of my invention.

Such refractory inorganic oxides which are contemplated for the present invention include crystalline aluminosilicate zeolites, such as mordenite, and faujasite-alumina, silica-alumina, silica-magnesia, silica-zirconia, silica-thoria, silica-berylia, silica-titania as well as ternary compositions, such as silica-alumina-thoria, silica-alumina-zirconia, silica-alumina-magnesia and silica-magnesia-zirconia.

Regardless of which refractory inorganic is selected for admixture with the silicalite, it must be resistant to the temperature and other conditions employed during the use of the catalyst composite. Such refractory inorganic oxide matrix material may also include synthetic or naturally occuring substances as well as clays, silica and/or metal oxides. The latter may be either naturally occuring or in the form of gelatinous precipitates or gels including mixtures of silica and metal oxides. Naturally occuring clays which can be composited with the silicalite include those of the montmorillonite and kaolin families, which families include the sub-bentenites and the kaolins commonly known as Dixie, McNamee-Georgia and Florida clays or others in which the main mineral constituted is halloysite, kaolinite, dickite, nacrite or anauxite. Such clays can be used in the raw state as originally mined or initially subjected to calcination, acid treatment or chemical modification.

The silicalite may be composited with the refractory inorganic oxide in any convenient method known in the prior art. For example one method for preparing the catalyst composition is by mixing the finely divided silicalite into an alumina sol, gelling the sol by addition of dilute ammonia to produce a gel which is then dried and pelleted. Spherical catalyst particles can be formed, for example, by dropping the admixture of finely divided silicalite and alumina sol together with a gelling agent into an oil bath to form spherical particles of an alumina gel containing silicalite. The silicalite and a refractory inorganic oxide can also be formed in any other desired shape or type of catalyst known to those skilled in the art such as rods, pills, pellets, tablets, granules, extrudates and the like forms. While any suitable refractory inorganic oxide may be utilized in my invention, the results may not necessarily be equivalent.

Alumina is a preferred refractory inorganic oxide for use herein. The alumina may be any of the various hydrous aluminum oxides or alumina gels such as alpha-alumina monohydrate of the boehmite structure, alpha-alumina trihydrate of the gibbsite structure, beta-alumina trihydrate of the bayerite structure, and the like. A particularly preferred alumina is referred to as Ziegler alumina and has been characterized in U.S. Pat. Nos. 3,852,190 and 4,012,313 as a byproduct from a Ziegler higher alcohol synthesis reaction as described in Ziegler's U.S. Pat. No. 2,892,858. For purposes of simplification, the name "Ziegler alumina" is used herein to identify this material. It is presently available from the Conoco Chemical Division of Continental Oil Company under the trademark Catapal. This material is an extremely high purity alpha-alumina monohydrate (boehmite) which after calcination at a high temperature has been shown to yield a high purity gamma-alumina.

The catalyst composite of the present invention preferably contains from about 5 weight percent to about 95 weight percent Ziegler alumina and from about 5 weight percent to about 95 weight percent silicalite. Regardless of the method preparing the admixture of silicalite and a refractory inorganic oxide, the composition is preferably calcined to form a catalytic composite. The calcination is suitably performed in air atmosphere at a temperature from about 425° C. to about 750° C., preferably at a temperature of from about 475° C. to about 550° C. over a period of from about 0.5 to about 10 hours.

Optional ingredients for the catalyst composite of the present invention may be selected from Group IV-A, V-B, V-A, VI-B, VII-A, VII-B and VIII of the Periodic Table of the Elements. More specifically the optional ingredients which may be incorporated with the catalyst of the present invention are germanium, tin, lead, vanadium, columbium, tantalum, phosphorous, arsenic, antimony, bismuth, chromium, molybdenum, tungsten, manganese, technetium, rhenium, fluorine, chlorine, bromine, iodine, iron cobalt, nickel, ruthenium, rhodium, palladium, osmium, iridium and platinum.

These optional ingredients may be incorporated in the catalytic composite in any suitable manner known to result in a relatively uniform distribution of the ingredients such as coprecipitation or cogellation, coextrusion, ion exchange or impregnation. A suitable method of introducing an optional ingredient involves the utilization of a soluble compound to impregnate the catalytic composite. Another acceptable procedure for incorporation of an optional ingredient is by adding the ingredient or a compound thereof to the initial step of compounding the silicalite and refractory inorganic oxide.

Suitable optional ingredients and their methods of incorporation are selected to enhance the desired characteristics of the finished catalyst depending upon the type of hydrocarbon conversion process which utilizes the catalyst. Not all ingredients and incorporation methods will give equivalent results.

Regardless of the details of how the optional components are combined with the catalyst of the present invention, the final catalyst generally will be dried at a temperature of about 100° C. to about 300° C. for a period of typically about 1 to about 24 hours or more and finally calcined or oxidized at a temperature of about 350° C. to about 700° C. in an air or oxygen atmosphere for a period of about 0.5 to about 10 or more hours.

According to one embodiment of the present invention, a hydrocarbon charge stock is contacted with a catalyst composite comprising silicalite and a refractory inorganic oxide in a hydrocarbon conversion zone. This contacting may be accomplished by using the catalyst in a fixed bed system, a moving bed system, a fluidized bed system or in a batch type operation; however, in view of the danger of attrition losses of the catalyst and of well known operational advantages, it is preferred to use either a fixed bed system or a dense-phase moving bed system. In a fixed bed system, the charge stock is preheated by any suitable heating means to the desired reaction temperature and then passed into a conversion zone containing a fixed bed of the catalyst composite. It is, of course, understood that the conversion zone may be one or more separate reactors with suitable means therebetween to ensure that the desired conversion temperature is maintained at the entrance to each reactor. It is also important to note that the reactants may be contacted with the catalyst bed in either upward, downward, or radial flow fashion. In addition, the reactants may be in the liquid phase, a mixed liquid-vapor phase, or a vapor phase when they contact the catalyst.

In the case where the catalyst of the present invention is used in a reforming operation, the reforming system will typically comprise a reforming zone containing one or more fixed beds or dense-phase moving beds of the catalyst. In a multiple bed system, it is, of course, within the scope of the present invention to use the present catalyst in less than all of the beds with a conventional catalyst being used in the remainder of the beds. This reforming zone may be one or more separate reactors with suitable heating means therebetween to compensate for the endothermic nature of the reactions that take place in each catalyst bed. The hydrocarbon feed stream that is charged to this reforming system will comprise hyrocarbon fractions containing naphthenes and paraffins that boil within the gasoline range. The preferred charge stocks are those consisting essentially of naphthenes and paraffins, although in some cases aromatics and/or olefins may also be present. This preferred class includes straight run gasolines, natural gasolines, synthetic gasolines, partially reformed gasolines and the like. On the other hand, it is frequently advantageous to charge thermally or catalytically cracked gasolines or higher boiling fractions thereof. Mixtures of straight run and cracked gasolines can also be used to advantage. The gasoline charge stock may be a full boiling gasoline having an initial boiling point of from about 50° F. to about 150° F. and an end boiling point within the range of from about 325° F. to about 425° F., or may be a selected fraction thereof which generally will be a higher boiling fraction commonly referred to as a heavy naphtha—for example, a naphtha boiling in the range of $C_7$ to 400° F. In some cases, it is also advantageous to charge pure hydrocarbons or mixtures of hydrocarbons that have been extracted from hydrocarbon distillates—for example, straight-chain paraffins—which are to be converted to aromatics. It is preferred that these charge stocks be treated by conventional catalytic pretreatment methods such as hydrorefining, hydrotreating, hydrodesulfurization, etc., to remove substantially all sulfurous, nitrogenous, and water-yielding contaminants therefrom and to saturate any olefins that may be contained therein.

In other hydrocarbon conversion embodiments, the charge stock will be of the conventional type customarily used for the particular kind of hydrocarbon conversion being effected. For example, in a typical isomerization embodiment, the charge stock can be a paraffinic stock rich in $C_4$ to $C_8$ normal paraffins, or a normal butane-rich stock, or an n-hexane-rich stock, or a mixture of xylene isomers, or an olefin-containing stock, etc. In a dehydrogenation embodiment, the charge stock can be any of the known dehydrogenatable hydrocarbons such as an aliphatic compound containing 2 to 30 carbon atoms per molecule, a $C_4$ to $C_{30}$ normal paraffin, a $C_8$ to $C_{12}$ alkylaromatic, a naphthene, and the like. In hydrocracking embodiments, the charge stock will be typically a gas oil, heavy cracked cycle oil, etc. In addition, alkylaromatics, olefins, and naphthenes can be conveniently isomerized by using the catalyst of the present invention. Likewise, pure hydrocarbons or substantially pure hydrocarbons can be converted to more valuable products by using the catalyst of the present invention.

The operating conditions utilized in the numerous hydrocarbon conversion embodiments of the present invention are in general those customarily used in the art for the particular reaction, or combination of reactions, that is to be effected. For instance, alkylaromatic, olefin, and paraffin isomerization conditions include a temperature of about 32° F. to about 900° F. and preferably from about 75° F. to about 600° F., a pressure of atmospheric to about 100 atmospheres, a hydrogen to hydrocarbon mole ratio of about 0.5:1 to about 20:1, and an LHSV (calculated on the basis of equivalent liquid volume of charge stock contacted with the catalyst per hour divided by the volume of the conversion zone containing catalyst and expressed in units of $hr^{-1}$) of about 0:2 to about 10. Dehydrogenation conditions include a temperature of about 700° F. to about 1250° F., a pressure of about 0.1 to about 10 atmospheres, a LHSV of about 1 to about 40 and a hydrogen to hydrocarbon mole ratio of about 1:1 to about 20:1. Likewise, typical hydrocracking conditions include a pressure of about 500 psig to about 3000 psig, a temperature of about 400° F. to about 900° F., a LHSV of about 0.1 to about 10 and hydrogen circulation rates of about 100 to about 10,000 SCF per barrel of charge.

In the reforming embodiment of the present invention, the pressure utilized is selected from the range of about 10 psig to about 1000 psig, with the preferred pressure being about 50 psig to about 600 psig. Particularly good results are obtained at low or moderate pressure; namely, a pressure of about 100 to about 400 psig.

The temperature required for reforming is in the range of from about 775° F. to about 1100° F. and preferably about 850° F. to about 1050° F. As is well known to those skilled in the continuous reforming art, the initial selection of the temperature within this broad range is made primarily as a function of the desired octane of the product reformate considering the characteristics of the charge stock and of the catalyst. Ordinarily, the temperature then is thereafter slowly increased during the run to compensate for the inevitable deactivation that occurs to provide a constant octane product.

The reforming embodiment of the present invention also typically utilizes sufficient hydrogen to provide an amount of about 1 to about 20 moles of hydrogen per mole of hydrocarbon entering the reforming zone, with excellent results being obtained when about 2 to about 6 moles of hydrogen are used per mole of hydrocarbon. Likewise, the liquid hourly space velocity (LHSV) used in reforming is selected from the range of about 0.1 to about 10, with a value in the range of about 1 to about 5 being preferred.

The isomerization embodiment of the present invention is suitable for the isomerization of straight chain or mildly branched chain paraffins containing 4 or more carbon atoms per molecule such as normal butane, normal pentane, normal hexane, normal heptane, normal octane, etc., and mixtures thereof. Cycloparaffins applicable are those containing at least 5 carbon atoms in the ring such as alkylcyclopentanes and cyclohexanes, including, methylcyclopentane, dimethylcyclopentane, cyclohexane, methylcyclohexane, dimethylcyclohexane, etc. This process also applies to the conversion of mixtures of paraffins and/or naphthenes such as those derived by selective fractionation and distillation of straight-run natural gasolines and naphthas. Such mixtures of paraffins and/or naphthenes include the so-called pentane fractions, hexane fractions and mixtures thereof. It is not intended, however, to limit this invention to these enumerated saturated hydrocarbons and it is contemplated that straight or branched chain hydrocarbons and naphthenes containing up to about 20 carbon atoms per molecule may be isomerized according to the process of the present invention with $C_4$–$C_9$ acyclic saturated hydrocarbons and $C_5$–$C_9$ cycloparaffins being particularly preferred.

The olefins applicable within this isomerization process are generally a mixture of olefinic hydrocarbons of approximately the same molecular weight, including the 1-isomer, 2-isomer and other position isomers, capable of undergoing isomerization to an olefin in which the double bond occupies a different position in the hydrocarbon chain. The process of this invention can be used to provide an olefinic feedstock for motor fuel alkylation purposes containing an optimum amount of the more centrally located double bond isomers, by converting the 1-isomer, or other near-terminal-position isomer into olefins wherein the double bond is more centrally located in the carbon atoms chain. The process of this invention is applicable to the isomerization of such isomerizable olefinic hydrocarbons as 1-butene to 2-butene or 3-methyl-1 butene to 2-methyl-2 butene. The process of this invention can be utilized to shift the double bond of an olefinic hydrocarbon such as 1-pentene, 1-hexene, or 4-methyl-1-pentene to a more centrally located position so that 2-pentene, 2-hexene, 3-hexene or 4-methyl-2-pentene, respectively, can be obtained. It is not intended to limit this invention to the enumerated olefinic hydrocarbons. It is contemplated that shifting the double bond to a different position may be effective in straight or branched chain olefinic hydrocarbons containing from 4 up to about 20 carbon atoms per molecule. The process of this invention also applies to the hydroisomerization of olefins wherein olefins are converted to branched-chain paraffins and/or branched olefins.

The process of this invention is also applicable to the isomerization of isomerizable alkylaromatic hydrocarbons, e.g., ortho-xylene, meta-xylene, para-xylene, ethylbenzene, the ethyltoluenes, the trimethylbenzenes, the diethylbenzenes, the triethylbenzenes, normal propylbenzene, isopropylbenzene, etc., and mixtures thereof. Preferred isomerizable alkylaromatic hydrocarbons are the alkylbenzene hydrocarbons, particularly the $C_8$ alkylbenzenes, and non-equilibrium mixtures of various $C_8$ aromatic isomers. Higher molecular weight alkylaromatic hydrocarbons such as the alkylnaphthalenes, the alkylanthracenes, the alkylphenanthrenes, etc., are also suitable.

The isomerizable hydrocarbons may be utilized as found in selective fractions from various naturally-occurring petroleum streams, e.g., as individual components or as certain boiling range fractions obtained by the selective fractionation and distillation of catalytically cracked gas oil. The process of this invention may be utilized for complete conversion of isomerizable hydrocarbons when they are present in minor quantities in various fluid or gaseous streams. The isomerizable hydrocarbons for use in the process of this invention need not be concentrated. For example, isomerizable hydrocarbons appear in minor quantities in various refinery offstreams, usually diluted with gases such as hydrogen, nitrogen, methane, ethane, propane, etc. These offstreams, containing minor quantities of isomerizable hydrocarbons, are obtained from various refinery installations, including thermal cracking units, catalytic cracking units, thermal reforming units, coking units, polymerization units, dehydrogenation units, etc., and have in the past been burned as fuel, since an economical process for the utilization of the hydrocarbon content has not been available. This is particularly true of refinery fluid streams which contain minor quantities of isomerizable hydrocarbons. The process of this invention allows the isomerization of aromatic streams such as reformate to produce xylenes, particularly paraxylene, thus upgrading the reformate from its gasoline value to a high petrochemical value.

An optional ingredient for the catalyst of the present invention is a Friedel-Crafts metal halide component. This ingredient is particularly useful in hydrocarbon conversion embodiments of the present invention wherein it is preferred that the catalyst utilized has a strong acid or cracking function associated therewith—for example, an embodiment wherein hydrocarbons are to be hydrocracked or isomerized with the catalyst of the present invention.

Suitable metal halides of the Friedel-Crafts type include aluminum chloride, aluminum bromide, ferric chloride, ferric bromide, zinc chloride, and the like compounds, with the aluminum halides and particularly aluminum chloride ordinarily yielding best results. Generally, the optional ingredient can be incorporated into the composite of the present invention by any of the conventional methods for adding metallic halides of this type; however, best results are ordinarily obtained when the metallic halide is sublimed onto the surface of the carrier material according to the preferred method disclosed in U.S. Pat. No. 2,999,074. The component can generally be utilized in any amount which is catalytically effective, with a value selected from the range of about 1 to about 100 weight percent of catalyst composite support generally being preferred.

A suitable catalytic composite for the isomerization of hydrocarbon comprises silicalite and alumina. In a preferred method, wherein the silicalite and alumina composite is impregnated with a Friedel-Crafts metal halide component, the presence of chemically combined hydroxyl groups in the alumina allows a reaction to occur between the Friedel-Crafts metal halide and the hydroxyl group of the carrier material. For example, aluminum chloride reacts with the hydroxyl groups of the carrier material to yield $Al-O-Al\ Cl_2$ active centers which enhance the catalyst behavior of the composite.

The Friedel-Crafts metal halide may be impregnated onto the catalyst composite containing combined hydroxyl groups by the sublimation of the Friedel-Crafts metal halide onto the composite under conditions such that the sublimed Friedel-Crafts metal halide is combined with the hydroxyl groups of the composite. For example, in the case of subliming aluminum chloride, which sublimes at about 184° C., suitable impregnation temperatures range from about 190° C. to about 700° C. with a preferable range being between 200° C. and about 600° C. The sublimation can be conducted at atmospheric pressure or under increased pressure and in the presence or absence of diluent gases such as hydrogen or light paraffinic hydrocarbons or both. The impregnation of the Friedel-Crafts metal halide may be conducted batch/wise, but a preferred method for impregnating the composite is to pass sublimed $Al_3$ vapors, in admixture with a carrier gas such as hydrogen, through a catalyst bed.

The amount of Friedel-Crafts metal halide combined with the composite may range from about 1 to up to about 100 weight of Friedel-Crafts metal halide-free composite. The final composite containing the sublimed Friedel-Crafts metal halide is treated to remove the unreacted Friedel-Crafts metal halide by subjecting the composite to a temperature above the sublimation temperature of the Friedel-Crafts metal halide for a time sufficient to remove from the composite any unreacted Friedel-Crafts metal halide. In the case of $AlCl_3$, temperatures of about 400° C. to about 600° C., and times of from about 1 to about 48 hours are sufficient.

Regardless of the details of how the components of the catalyst are combined, the final catalyst will be dried at a temperature of about 200° F. to about 600° F. for a period of typically about 1 to about 24 hours or more and finally calcined or oxidized at a temperature of about 700° F. to about 1100° F. in an air or oxygen atmosphere for a period of about 0.5 to about 10 or more hours.

The following examples are given to illustrate further the preparation of the catalytic composite of the present invention and the use thereof in the conversion of hyrocarbons. It is understood that the examples are intended to be illustrative rather than restrictive.

EXAMPLE I

A 50/50 blend of a silica polymorph consisting of crystalline silica, said silica polymorph after calcination in air at 600° C. for one hour, having a mean refractive index of $1.39 \pm 0.01$ and a specific gravity at 25° C. of $1.70 \pm 0.05$ g/cc (silicalite) and Ziegler alumina was blended and peptized using a 5% nitric acid solution. The peptized blend was then extruded and pelletized to form catalyst particles which were calcined.

EXAMPLE II

A portion of the calcined catalyst particles from Example I was loaded into a continuous flow, fixed bed pilot plant used for the isomerization of aromatic hydrocarbons. The feedstock, as described in Table I, was commingled with about 3.8 moles of hydrogen per mole of hydrocarbon, heated to about 700° F. and continuously charged at a 2 $hr^{-1}$ liquid hourly space velocity (LHSV) to the reactor which was maintained at 100 psig.

TABLE I

| FEEDSTOCK COMPOSITION, MOLE % | |
| --- | --- |
| Benzene | 0.137 |
| Toluene | 0.349 |
| Ethyl Benzene | 28.333 |
| p-Xylene | 2.420 |
| m-Xylene | 55.456 |
| o-Xylene | 4.436 |
| $C_8$ Naphthenes | 5.199 |
| $C_9$ Naphthenes | 0.356 |
| $C_8$ Paraffins | 1.078 |
| $C_9$ Paraffins | 2.237 |

The resulting isomerized liquid product was recovered and analyzed. A summary of product inspection is presented in Table II.

TABLE II

| PRODUCT INSPECTION, MOLE % | |
| --- | --- |
| Benzene | 5.6 |
| Toluene | 1.2 |
| Ethyl Benzene | 18.4 |
| p-Xylene | 13.7 |
| m-Xylene | 35.8 |
| o-Xylene | 11.5 |
| $C_9$ Aromatic | 1.1 |
| $C_8$ Naphthenes | 4.8 |
| $C_9$ Paraffins | 1.9 |
| $C_{10}$ Aromatics | 4.0 |

TABLE II-continued

| PRODUCT INSPECTION, MOLE % | |
| --- | --- |
| Other | 2.0 |

This catalyst at 700° F. and 100 psig exhibits very good xylene isomerization with a mole ratio of p-xylene to total xylenes of 22.4%. Additionally, the catalyst displays an extraordinary ability to preferentially transalkylate and dealkylate ethylbenzene rather than xylenes. In other words, the mole percentage of the ethyl benzene has decreased from 28.3 in the feedstock to 18.4 in the product. While the mole percentage decrease in total xylenes was from 62.3 to 61. This preferential transalkylation and dealkylation is a highly valued characteristic of a catalyst utilized in a petrochemical complex where ethylbenzene disappearance is required while maintaining xylenes.

I claim:

1. A catalyst composite comprising from about 5 weight percent to about 95 weight percent of a silica polymorph consisting of crystalline silica, said silica polymorph after calcination in air at 600° C. for one hour, having a mean refractive index of 1.39±0.01 and a specific gravity at 25° C. of 1.70±0.05 g/cc and at least 5 weight percent to about 95 weight percent Ziegler alumina.

2. The catalytic composite of claim 1 which comprises a component selected from Group IV-A, V-B, V-A, VI-B, VII-A, VII-B and VIII.

* * * * *

Notice of Adverse Decision in Interference

In Interference No. 101,226, involving Patent No. 4,362,653, D. W. Robinson, HYDROCARBON CONVERSION CATALYST, final judgment adverse to the patentee was rendered Aug. 5, 1985, as to claims 1 and 2.
*[Official Gazette November 26, 1985.]*